United States Patent [19]

Abe et al.

[11] Patent Number: 5,110,739
[45] Date of Patent: May 5, 1992

[54] PROCESS FOR SELECTIVE FERMENTATION WITH MUTANTS OF *PEDIOCOCCUS HALOPHILUS*

[75] Inventors: Keietsu Abe, Noda; Kinji Uchida, Nagareyama, both of Japan

[73] Assignee: Kikkoman Corporation, Noda, Japan

[21] Appl. No.: 733,065

[22] Filed: Jul. 17, 1991

Related U.S. Application Data

[63] Continuation of Ser. No. 163,627, Mar. 3, 1988, abandoned.

[30] Foreign Application Priority Data

Mar. 7, 1987 [JP] Japan .................................. 62-51210

[51] Int. Cl.$^5$ .......................... C12N 1/00; C12N 1/20; C12P 1/00
[52] U.S. Cl. ..................... 435/252.9; 435/41; 435/253.6; 435/822
[58] Field of Search ..................... 435/252.9, 194, 822, 435/41, 253.6; 426/46, 18

[56] References Cited

U.S. PATENT DOCUMENTS

| | | | |
|---|---|---|---|
| 4,308,284 | 12/1981 | Noda et al. | 426/7 |
| 4,508,738 | 4/1985 | Gonzalez | 435/252.9 |
| 4,587,127 | 6/1986 | Akao et al. | 426/47 |
| 4,722,846 | 2/1988 | Abe et al. | 426/46 |

FOREIGN PATENT DOCUMENTS 51-19797 1/1976 Japan .
5878564 11/1981 Japan .

OTHER PUBLICATIONS

*Bergey's Manual of Systematic Bacteriology*, vol. 2, 1986, p. 1075.
Saier et al., Permeose-Specific Mutations in *Salmonella typhimurium* and *Escherichia coli* That Release the Glycerol, Maltose, Melibiose and Lactose Transport Systems from Regulation by the Phosphoenolpyruvate: Sugar Phototransferase System, J. of Bacteriology, vol. 133, 1978, pp. 1358-1367.
Romano et al., Distribution of the Phosphoenolpyruvate: Glucose Phototransferase System in Fermentative Bateria, J. of Bacteriology, vol. 139, 1979, pp. 93-97.
Uchida, Proc. of the 10th Symposium on Brewage.
Bull. Agr. Chem. Soc. Japan, vol. 22, pp. 353-362, 1958.
Hamilton, et al., (1978), J. Bacteriol., 136:900-908.
Liberman, et al., (1984), Infect. Immunity, 43:536-542.
Vadeboncoeur (1984), Can. J. Microbiol., 30:495-502.

*Primary Examiner*—David M. Naff
*Assistant Examiner*—Susan M. Weber
*Attorney, Agent, or Firm*—Banner, Birch, McKie & Beckett

[57] ABSTRACT

A process is provided for selective fermentation with microorganisms belonging to the Genus Pediococcus and having reduced or no phosphoenolypyruvate dependent sugar:phosphotransferase system. The microorganism is capable of fermenting a medium containing a metabolite which induces catabolite repression and a metabolite whose catabolism is inhibited by catabolite repression. The metabolite which induces catabolite repression may be selected from glucose and mannose and the metabolite whose catabolism is inhibited by catabolite repression may be selected from arabinose, xylose, galactose, sucrose, maltose, trehalose, lactose, and glycerin. The Pediococcus microorganisms used in this process are mutant strains designated *Pediococcus halophilis* I-1, having an accession number FERM BP-1303, and *Pediococcus halophilis* I-2, having an accession number FERM BP-1304.

8 Claims, No Drawings

PROCESS FOR SELECTIVE FERMENTATION WITH MUTANTS OF *PEDIOCOCCUS HALOPHILUS*

This application is a continuation of application Ser. No. 07/163,627, filed Mar. 3, 1988, now abandoned.

BACKGROUND OF THE INVENTION

1. Field of the Invention

The present invention relates to a process for selective fermentation.

2. Description of the Prior Art

When more than two substrates are to be metabolized by certain microorganisms, one that is readily-utilizable by the organism represses induction of the enzyme responsible for catabolism of the other substrate. This phenomenon is known as "Catabolite repression" [Hartwell, L. and B. Magasanik; J. Mol. Biol. 7, 401–420 (1963): Monod, J.; Recherches sur la croissance des cultures bacteriennes, thesis, Harman, Paris, 145 (1942)].

The above phenomenon is observed when microorganisms belonging to the Genus Pediococcus, such as *Pediococcus halophilus*, are cultivated in a medium containing more than two utilizable substrates as an energy source.

It has been known that catabolite repression as described above is observed in metabolism of not only substrates of energy sources for the microorganisms, including sugars, amino acids (e.g. arginine) and organic acids, but also in the metabolism of macromolecules such as nucleic acids, polysaccharides and proteins.

Thus, in general, there are many cases where some substrates are not utilized because of repression of the biosynthesis of their metabolic enzymes when readily-utilizable sugars, such as glucose and mannose, are present; or where desired enzymes are not produced.

Catabolite repression is one of the most powerful systems for metabolic regulation in Pediococcus, which becomes a problem in selective fermentation of the non-readily utilizable substrates as well as in production of certain enzymes or secondary metabolites. It has been almost impossible to release this repression. Only possible means are to cultivate for a very long period of time or to remove the substrate in the medium which is inhibitory to the selective fermentation. However, such fermentation requires additional cost or limits the use of natural medium which is cheap but has complicated composition.

Under the circumstances, the present inventors sought earnestly for efficient methods to release catabolite repression in microorganisms belonging to *Pediococcus halophilus* and found that phosphoenolpyruvate dependent sugar:phosphotransferase system (PTS) is present in these organisms and that catabolite repression can be released by inhibiting PTS.

PTS is the sugar transport system known in enteric bacteria, which was described by Kundig, W. et al. in Proc. Natl. Acad. Sci., U.S.A., 52, 1067–1074 (1964) and by P. W. Postma et al. in Microbiol. Rev., 49, 232–269 (1985). However, PTS has not been reported so far in Pediococcus.

SUMMARY OF THE INVENTION

The present inventors studied intensively to induce and isolate mutants of *Pediococcus halophilus* with reduced or no PTS activities, and were able to select the mutants with the desired characteristics. It was also found that such mutants, when inoculated and cultured in a medium containing a metabolic substrate which induces catabolite repression and one whose catabolism is inhibited by catabolite repression together with other nutrients if necessary, can selectively ferment the latter substrate and remove it from the fermentation broth. Thus, the present invention has been accomplished.

The present invention is concerned with a process for selective fermentation which comprises inoculating and cultivating in a medium microorganisms belonging to the Genus Pediococcus and having reduced or no activity of phosphoenolpyruvate dependent sugar: phosphotransferase system, which medium contains a metabolic substrate inducing catabolite repression and a metabolic substrate whose catabolism is inhibited by catabolite repression, and other nutrients if necessary.

DETAILED DESCRIPTION OF THE INVENTION

A novel mutant strain of *Pediococcus halophilus* of the present invention which is defective in PTS is, for example, *Pediococcus halophilus* I-1, and a novel mutant strain of the present invention which has low PTS activity is, for example, *Pediococcus halophilus* I-2.

*Pediococcus halophilus* I-1 is completely released from catabolite repression, and thus is a more preferable strain to *Pediococcus halophilus* I-2.

Both of the above strains, *Pediococcus halophilus* I-1 and I-2, are novel mutants obtained by mutagenesis of a wild strain of *Pediococcus halophilus* I isolated from soy source moromi. *Pediococcus halophilus* I, I-1 and I-2 have the following microbiological characteristics. The characteristics are described according to Bergey's Manual of Determinative Bacteriology, 8th ed. (1974).

Characteristics of *Pediococcus halophilus* I:

(a) Morphology [stationarily grown in bouillon medium supplemented with xylose 1.0% (w/v), yeast extract 0.5% (w/v) and sodium chloride 5% (w/v) at 30° for 72 hours]
  (1) Shape and size of the cell:
    Spheres, 0.6–0.8 µm in diameter, occuring in tetrad with some in pairs.
  (2) Polymorphism: none
  (3) Motility: none
  (4) Sporulation: none
  (5) Gram-staining: positive
  (6) Acid fast: none (b) Cultural characteristics
  (1) Bouillon agar plate: No growth on surface, white pin-head colony inside. No pigment formation.
  (2) Bouillon agar slant: No growth on surface.
  (3) Bouillon broth: Uniform turbidity throughout medium, forms white precipitate. No growth on surface.
  (4) Bouillon gelatin stab: Uniform growth along stab; gelatin not liquefied.
  (5) Litmus milk: Neutral, tentatively decolored.

(c) Physiological characteristics
  (1) Nitrate reduction: negative
  (2) Denitrification: negative
  (3) Methyl red (MR) test: negative
  (4) Voges-Proskauer (VP) test: negative
  (5) Indole: not produced
  (6) Hydrogen sulfide: not produced
  (7) Starch: not hydrolyzed
  (8) Citric acid: not utilized
  (9) Inorganic nitrogen: not utilized

(10) Pigments: not produced
(11) Urease: not produced
(12) Oxidase: negative
(13) Catalase: negative
(14) Range for growth: pH 5.5-9.0, with optimum pH of 7.0; 20°-30° C., no growth at 45° C. or above
(15) Facultative anaerobic, prefers anaerobic conditions
(16) O-F test (supplemented with yeast extract): Fermentative
(17) Production of acid and gas from sugars:

|    | acid production | gas production |
|---|---|---|
| 1) L-arabinose | + | − |
| 2) D-xylose | + | − |
| 3) D-glucose | + | − |
| 4) D-mannose | + | − |
| 5) D-fructose | + | − |
| 6) D-galactose | + | − |
| 7) maltose | + | − |
| 8) sucrose | + | − |
| 9) lactose | − | − |
| 10) trehalose | + | − |
| 11) D-sorbit | − | − |
| 12) D-mannit | + | − |
| m 13) inosit | − | − |
| 14) glycerin | + | − |
| 15) starch | − | − |

(d) Other characteristics
  (1) Production of lactic acid and acetic acid from sugars
  (2) No decomposition of arginine
  (3) Grows best in presence of 5-6% NaCl; grows in presence of 20% NaCl; high resistance to NaCl.

Based on the characteristics of high tolerance to NaCl and growth range of pH between 5.5 and 9.0, the newly isolated strain was classified into *Pediococcus halophilus*.

The strain *Pediococcus halophilus* I was deposited at the Fermentation Research Institute, the Agency of Industrial Science and Technology on Feb. 24, 1987 under the Budapest Treaty and the accession number FERM BP-1302 was given to it.

Characteristics of *Pediococcus halophilus* I-1:
Microbiological characteristics of *Pediococcus halophilus* I-1 are identical to that of *Pediococcus halophilus* I, except in (17) Production of acid and gas from sugars, which is given in the following table, and difference in PTS activity as shown in Table 1.

|    | acid production | gas production |
|---|---|---|
| 1) L-arabinose | + | − |
| 2) D-xylose | + | − |
| 3) D-glucose | − | − |
| 4) D-mannose | − | − |
| 5) D-fructose | + | − |
| 6) D-galactose | + | − |
| 7) maltose | + | − |
| 8) sucrose | + | − |
| 9) lactose | − | − |
| 10) trehalose | + | − |
| 11) D-sorbit | − | − |
| 12) D-mannit | + | − |
| 13) inosit | − | − |
| 14) glycerin | + | − |
| 15) starch | − | − |

Characteristics of *Pediococcus halophilus* I-2:
Microbiological characteristics of *Pediococcus halophilus* I-2 are identical to those of *Pediococcus halophilus* I except PTS activities when grown on glucose or mannose as shown in Table 1.

Determination of PTS activities was based on the procedure described by Kornberg, H. L. et al., Biochem. J. 128, 1345-1352 (1972).

TABLE 1

| Strain | PTS Relative activity (%) |
|---|---|
| *Pediococcus halophilus* I | 100 |
| *Pediococcus halophilus* I-1 | 0 |
| *Pediococcus halophilus* I-2 | 15 |

*Pediococcus halophilus* I-1 and *Pediococcus halophilus* I-2 are considered to be novel mutant strains due to the loss or reduction, respectively, of PTS activity.

*Pediococcus halophilus* I-1 and *Pediococcus halophilus* I-2 were deposited under the Budapest Treaty at the Fermentation Research Institute, the Agency of Industrial Science and Technology on Feb. 24, 1987 under the accession numbers of FERM BP-1303 and FERM BP-1304, respectively.

The microorganisms according to the present invention are not limited to the above described strains. Reduction or loss of PTS activity may result in changes in fermentation characteristics of major sugars, and thus mutants will appear, which may not be classified into *Pediococcus halophilus*. However, those mutant strains are also within the scope of the present invention as far as they are derived from a parent strain belonging to *Pediococcus halophilus* and possess low or no PTS activities.

Moreover, not only the mutants obtained by artificial mutagenesis but also mutants isolated by natural mutation as PTS defective strains are included in the microorganism according to the present invention.

Mutagenesis may be effected by treatment with, for example, mutation inducing agents such as N-methyl-N'-nitro-N-nitrosoguanidine (MNNG), ethyl methane sulfonate and methyl methane sulfonate, ultraviolet irradiation, X-ray irradiation and radiation, and genetic engineering through transformation, transduction or mating using phages or plasmids.

Any medium generally used for cultivating the strains of *Pediococcus halophilus* may be used for cultivation of the novel mutant strains of the present invention.

As the nitrogen source, any nitrogen-containing compounds which are utilizable may be used alone or in combination, such as yeast extract, peptone, meat extract, gelatin, corn steep liquor, amino acids, soybean or flour extracts and the like. The medium preferably contains, in addition to the above nitrogen source, one or more of inorganic salts such as manganese, phosphate, potassium, magnesium and calcium salts, and other nutrients necessary for growth, carbon sources such as sugars, various organic and inorganic compounds, vitamins and the like. Furthermore, the medium preferably contains NaCl at a concentration between 2 and 17%. The medium may contain soy sauce moromi broth obtained from soy sauce manufacturing process which is diluted so as to give final NaCl concentration of about 15%.

The mutant strains of the present invention are preferably cultivated in a liquid medium, preferably under stationary culture or under anaerobic conditions. The range of the cultivation temperature is between 15° and 50° C., preferably between 20° and 40° C. The period of cultivation depends on the concentration of sodium chloride in the medium but is generally between 1 and 10 days. The pH range of the medium during the cultivation is between pH 3 and 9 both for synthetic media (such as MYP medium and YP medium) and soy sauce moromi broth medium.

For collecting the cells of the present mutants from the culture thus obtained, any conventional method may be used, for example, cells are collected by centrifugation or filtration followed by washing if necessary.

According to the present invention, the mutant strain is inoculated and cultivated in the medium containing a metabolic substrate inducing catabolite repression and a metabolic substrate whose catabolism is inhibited by catabolite repression, and other nutrients when necessary, by which the metabolic substrate whose catabolism is ordinary inhibited is selectively fermented.

The metabolic substrates which may induce catabolite repression are major sugars such as glucose and mannose. They are used singly or in combination.

The metabolic substrates whose catabolism may be inhibited by catabolite repression are pentoses such as arabinose and xylose; sugars such as galactose, sucrose, maltose, trehalose, and lactose; and other substances utilizable as an energy source by the microorganism concerned such as glycerin, polyols, amino acids and organic acids. Catabolism of these compounds are known to be inhibited when more readily utilizable sugar, such as glucose or mannose, is present. The compounds are used alone or in combination.

Any material may be used for the medium, which contains a metabolic substrate inducing catabolite repression and a metabolic substrate whose catabolism is inhibited by catabolite repression, for example soy sauce moromi broth or wood hydrolyzate.

As the nutrients, compounds selected from the above mentioned media compositions may be added to the medium in addition to a metabolic substrate inducing catabolite repression and a metabolic substrate whose catabolism is inhibited by catabolite repression.

The inoculum size of the present microorganism is, for example, $10^2$–$10^9$ cells/g or $10^2$–$10^9$ cells/ml, preferably between $10^4$–$10^6$ cells/g or $10^4$–$10^6$ cells/ml.

In the selective fermentation using the present microorganisms, major sugar such as glucose and mannose virtually remain after the fermentation or only a part of these sugars is consumed, while the substances whose catabolism is generally inhibited may be fermented and consumed completely or in part, and organic acids, mainly lactic acid and acetic acid, are produced. The extent of consumption depends on the strain and fermentation conditions used.

Fermentation conditions may be those where the substrates whose catabolism is generally inhibited by catabolite repression can be consumed through fermentation, for example the conditions similar to the above described for cultivation of the present mutant strains. Moreover, such fermentation conditions are also employed which do not necessarily support full growth of the organisms once they have reached to a certain level of growth as far as they can provide continuous catabolism by the present organisms.

Thus, according to the present invention, metabolic substrates whose catabolism is generally inhibited by catabolite repression may be selectively fermented and reduced or removed from the complex materials containing a metabolic substrate inducing catabolite repression and a metabolic substrate (or substrates) whose catabolism is inhibited by catabolite repression. By the conventional technology, this has been almost impossible due to catabolite repression which is universal to microorganisms. Exceptions have been some particular cases where fermentation is conducted for very long period of time, or the inhibitory substrate for selective fermentation is removed. Using the process according to the present invention, such fermentation becomes possible without additional costs and employing cheap natural medium containing complex mixtures. Thus, the present invention provides processes of particular industrial importance. The following examples are intended to illustrate the present invention in further detail.

EXAMPLE 1

Induction of mutant strains having no or reduced PTS activities by mutagenesis

*Pediococcus halophilus* I (FERM BP-1302) was inoculated in 5 ml of the medium given in Table 2 (designated as YPGA-1-5) and stationarily cultivated at 30° C. for 4 days.

TABLE 2

| Yeast extract | 0.3 g/100 ml |
| Polypeptone | 0.5 g/100 ml |
| Dipotassium phosphate | 0.5 g/100 ml |
| Sodium thioglycollate | 0.1 g/100 ml |
| Sodium chloride | 5.0 g/100 ml |
| Galactose | 1.0 g/100 ml |

The culture thus obtained was centrifuged at 18,000 rpm for 10 minutes to collect the cells, which were washed with 0.1M Tris-malate buffer containing 5% NaCl (TM buffer). They were resuspended in 5 ml of TM buffer to give the concentration of $10^8$ cells/ml. To the cell suspension was added MNNG at the concentration of 100 μg/ml and incubated at 30° C. for 30 minutes.

The incubation mixture was diluted with 100-fold volume of TM buffer and a 100 μl aliquot was used to inoculate YPGA-1-5 medium. Stationary cultivation was conducted at 30° C. for 4 days. The culture was diluted with 5% NaCl solution so as to give the cell density of $10^3$ cells/ml and 100 μl aliquots were used to inoculate the agar plates (MYPGA-1-5/CaCO₃ plates) with the composition shown in Table 3. The plates were anaerobically incubated at 30° C. for 9 days in a GAS-packed system (BBL Microbiology Systems).

Colonies grown on the MYPGA-1-5/CaCO$_3$ plates were transferred to the medium of Table 4 (YPGGA-1-5 medium) and incubated at 30° C. for 4 days to select strains with significant changes in galactose consumption.

TABLE 3

| Meat extract | 0.5 g/100 ml |
| Yeast extract | 0.5 g/100 ml |
| Polypeptone | 0.5 g/100 ml |
| Sodium thioglycollate | 0.1 g/100 ml |
| Calcium carbonate | 0.5 g/100 ml |
| Agar | 1.5 g/100 ml |
| Sodium chloride | 5.0 g/100 ml |
| Galactose | 1.0 g/100 ml |

TABLE 4

| Yeast extract | 0.3 g/100 ml |
| Polypeptone | 0.5 g/100 ml |
| Dipotassium phosphate | 0.5 g/100 ml |
| Sodium thioglycollate | 0.1 g/100 ml |
| NaCl | 5.0 g/100 ml |

TABLE 4-continued

| | |
|---|---|
| Glucose | 1.0 g/100 ml |
| Galactose | 1.0 g/100 ml |

Galactose content was determined according to the method described by H. U. Bergmeyer et al., in Methods of Enzymatic Analysis, 3rd ed., vol. 6, "Metabolites: Carbohydrates", 281–296 (1984), Verlag Chemie.

Strains selected by the cultivation in YPGGA-1-5 medium were analyzed for PTS activities as described above and novel mutant strains, *Pediococcus halophilus* I-1 (FERM BP-1303) and I-2 (FERM BP-1304) were obtained as shown in Table 1.

EXAMPLE 2

A loopful cells of the novel mutant strains, *Pediococcus halophilus* I-1 (FERM BP-1303) and I-2 (FERM BP-1304), obtained from Example 1 were inoculated in 5 ml each of YPGA-1-5 medium described in Example 1 and incubated at 30° C. for 4 days.

The cells were collected by centrifugation at 18,000 rpm for 10 minutes, washed with 5 ml of 5% NaCl solution and dried by the usual method to obtain 0.735 mg and 0.802 mg of dried cells of *Pediococcus halophilus* I-1 and *Pediococcus halophilus* I-2, respectively.

EXAMPLE 3

One loopful cells of each of *Pediococcus halophilus* I-1 (FERM BP-1303) and *Pediococcus halophilus* I-2 (FERM BP-1304) obtained by mutagenesis described in Example 1 were inoculated in 5 ml each of the medium of Table 5 (YPM-1-5) and stationarily cultivated at 30° C. for 4 days. The remaining sugars in the cultures were analyzed and the results are shown in Table 6.

Sugar contents of the cultures were determined according to the procedure described by Sinner, M. and Puls, J., J. Chromatogr. 156, 197 (1978).

TABLE 5

| | |
|---|---|
| Yeast extract | 0.3 g/100 ml |
| Polypeptone | 0.5 g/100 ml |
| Dipotassium phosphate | 2.0 g/100 ml |
| Sodium thioglycollate | 0.1 g/100 ml |
| Sodium chloride | 5.0 g/100 ml |
| Glucose | 5.0 g/100 ml |
| Mannose | 0.5 g/100 ml |
| Galactose | 0.5 g/100 ml |
| Arabinose | 0.5 g/100 ml |
| Xylose | 0.5 g/100 ml |

TABLE 6

| | Kind of sugars Remaining sugars (g/100 ml) | | | | |
|---|---|---|---|---|---|
| Strain | Galactose | Arabinose | Xylose | Glucose | Mannose |
| *Pediococcus halophilus* I (parent strain) | 0.5 | 0.4 | 0.5 | 3.92 | 0.21 |
| *Pediococcus halophilus* I-1 (present invention-1) | 0.1 | 0 | 0.2 | 4.96 | 0.49 |
| *Pediococcus halophilus* I-2 (present invention-2) | 0.35 | 0.15 | 0.4 | 4.61 | 0.43 |

As apparent from the result of Table 6, the strain of the present invention-2, when compared with the parent strain, catabolized well and selectively galactose, arabinose and xylose in the medium, and the strain of the present invention-1 exhibited marked and selective catabolism of galactose and xylose, and particularly of arabinose, in the medium compared with the parent strain.

EXAMPLE 4

100 kg of defatted soybeans which were steam denatured were mixed with 105 kg of wheat roasted and crushed, to which koji mold was inoculated, and they were incubated for 42 hours to obtain soy sauce koji.

360 l of a salt solution containing 90 kg of NaCl, which had been cooled to 15° C., was added to the above koji and they were transferred to a 600 l airtight tank.

After 3 weeks of incubation, aliquots were taken out and steri-filtered through a membrane filter having pore size of 0.22 μ (Japan Milipore Co.) to obtain soy sauce moromi solution. To each of 100 ml of the above solution was inoculated a loopful each of the novel mutant strains selected through mutagenesis as described in Example 1, *Pediococcus halophilus* I-1 (FERM BP-1303) and I-2 (FERM BP-1304), and *Pediococcus halophilus* I (FERM BP-1302) and incubated at 30° C. for 7 days to obtain cultures, respectively.

The remaining sugars in the cultures were analyzed and shown in Table 7. Sugar contents were determined according to the procedure of Sinner, M. and Puls, J., J. Chromatography, 156, 197 (1978).

TABLE 7

| | Kind of sugars Remaining sugars (g/100 ml) | | | | |
|---|---|---|---|---|---|
| Strain | Glucose | Galactose | Arabinose | Xylose | Mannose |
| *Pediococcus halophilus* I (parent strain) | 5.01 | 0.62 | 0.45 | 0.41 | 0.21 |
| *Pediococcus halophilus* I-1 (present invention-1) | 6.26 | 0.21 | 0 | 0.08 | 0.34 |
| *Pidiococcus halophilus* I-2 (present invention-2) | 5.77 | 0.46 | 0.15 | 0.37 | 0.31 |

As apparent from Table 7, the strain of the present invention-2, when compared with the parent strain, markedly and selectively consumed galactose, arabinose and xylose in the medium in the presence of high concentration of glucose. The strain of the present invention-1 also showed significantly higher and selective consumption of galactose and xylose, and arabinose, in particular, compared with the parent strain.

What is claimed is:
1. A process for selective fermentation, comprising:
(a) providing a medium containing at least one metabolite which induces catabolite repression, selected from the group consisting of glucose and mannose, and at least two metabolites whose catabolism is inhibited by catabolite repression, selected from the group consisting of arabinose, xylose, galactose, sucrose, maltose, trehalose, lactose, and glycerin;
(b) inoculating said medium with an inoculum containing an organism selected from the group consisting of *Pediococcus halophilis* I-2, having an accession number FERM BP-1304, and *Pediococcus*

*halophilis* I-1, having an accession number FERM BP-1303, (c) fermenting said inoculated medium for a fermentation period such that the concentration in said inoculated medium of each of said at least two metabolites whose catabolism is inhibited by catabolite repression is reduced, but such that said medium still contains said metabolite which induces catabolite repression.

2. A process for selective fermentation of claim 1, wherein said medium contains a material selected from the group consisting of soy sauce moroni and wood hydrolysates, said material containing said metabolite which induces catabolite repression and said metabolites whose catabolism is inhibited by catabolite repression.

3. A process for selective fermentation of claim 1, wherein the inoculum size of *Pediococcus halophilus* I-1, having an accession number FERM BP-1303, or *Pediococcus halophilus* I-2, having an accession number FERM BP-1304, is $10^2$–$10^9$ cells/g or cells/ml.

4. A process for selective fermentation of claim 1, wherein the inoculum size of *Pediococcus halophilus* I-1, having an accession number FERM BP-1303, or *Pediococcus halophilus* I-2, having an accession number FERM BP-1304, is $10^4$–$10^6$ cells/g or cells/ml.

5. A process for selective fermentation of claim 1, wherein the fermentation is conducted at a temperature range of 15°–50° C.

6. A process for selective fermentation of claim 1, wherein the fermentation is conducted at a temperature range of 20°–40° C.

7. A process for selective fermentation of claim 1, wherein the fermentation period is between 1–10 days.

8. A process for selective fermentation of claim 1, wherein the fermentation is conducted at a pH range of pH 3–9.

* * * * *